US010940100B2

(12) United States Patent
Carter et al.

(10) Patent No.: US 10,940,100 B2
(45) Date of Patent: Mar. 9, 2021

(54) COSMETIC COMPOSITION WITH LONG WEAR, METALLIC FINISH AND COOLING SENSATION

(71) Applicant: L'ORÉAL, Paris (FR)

(72) Inventors: Shirley Carter, Clark, NJ (US); Sonal Patel, Iselin, NJ (US); Lisa Ann Voorhees-Nordhaus, Middlesex, NJ (US)

(73) Assignee: L'ORÉAL, Paris (FR)

( * ) Notice: Subject to any disclaimer, the term of this patent is extended or adjusted under 35 U.S.C. 154(b) by 127 days.

(21) Appl. No.: 15/992,471

(22) Filed: May 30, 2018

(65) Prior Publication Data

US 2019/0365612 A1 Dec. 5, 2019

(51) Int. Cl.

| | |
|---|---|
| ***A61K 8/06*** | (2006.01) |
| ***A61K 8/89*** | (2006.01) |
| ***A61Q 1/02*** | (2006.01) |
| ***A61K 8/81*** | (2006.01) |
| ***A61K 8/25*** | (2006.01) |

(52) U.S. Cl.

CPC ................ *A61K 8/062* (2013.01); *A61K 8/25* (2013.01); *A61K 8/8152* (2013.01); *A61K 8/8158* (2013.01); *A61K 8/89* (2013.01); *A61Q 1/02* (2013.01)

(58) Field of Classification Search

None

See application file for complete search history.

(56) References Cited

U.S. PATENT DOCUMENTS

| | | | | |
|---|---|---|---|---|
| 2005/0048016 A1* | 3/2005 | Lebreton | A61K 8/8158 | 424/70.12 |
| 2006/0110346 A1 | 5/2006 | Lu | | |
| 2006/0130248 A1 | 6/2006 | Pays et al. | | |
| 2013/0039961 A1* | 2/2013 | Gonzales | A61K 8/8117 | 424/401 |
| 2013/0150457 A1* | 6/2013 | Feltin | A61K 8/4953 | 514/770 |

FOREIGN PATENT DOCUMENTS

| | | |
|---|---|---|
| WO | WO2016096627 A1 * | 6/2016 |
| WO | WO2017050699 A1 * | 3/2017 |

* cited by examiner

*Primary Examiner* — Robert A Wax
*Assistant Examiner* — Randeep Singh
(74) *Attorney, Agent, or Firm* — Meagher Emanuel Laks Goldberg & Liao, LLP.

(57) ABSTRACT

Disclosed is a long wearing cosmetic product with elegant glide and feel with cooling sensation and impactful color intensity with high coverage. The disclosed combination of a silicone resin, an ethylenic polymer including a monomer having a bicyclic group, and a taurate copolymer provides a flexible/soft film on eye lids which is not brittle and wears longer for hours.

20 Claims, No Drawings

COSMETIC COMPOSITION WITH LONG WEAR, METALLIC FINISH AND COOLING SENSATION

TECHNICAL FIELD

The present invention relates to a composition in the form of an oil-in-water (O/W) emulsion, more particularly to a cosmetic composition for making up and/or caring for the skin.

BACKGROUND

It is known practice, in the cosmetics or dermatological field, to develop emulsion products, including O/W emulsions. O/W emulsions consist of a fatty or oil phase dispersed in an aqueous phase, having an external aqueous phase. It is known that cosmetic/dermatological products based on the O/W emulsions are pleasant to use due to the feeling of freshness that the external aqueous phase can provide. However, cosmetic/dermatological products of this type are also easily removed from the skin due to water, perspiration, tears, etc.

Many cosmetic/dermatological products utilize a film former to prevent the ready removal of O/W emulsions. However, film formers often have characteristics which are not desirable in cosmetic or dermatological product, including stickiness, tackiness, and brittleness. Further, with certain products, other desired performance characteristics, such as allowing a user to evenly apply high levels of pigments on the skin or being compatible with materials that can provide a particular desired sensation on the skin, are needed. Conventional systems fail to meet those needs.

Thus, what is needed is a system for a cosmetic or dermatological product that provides long wear, the ability to handle high loads of pigment, and maintain compatibility with a range of sensates or sensation-providing cosmetic or dermatological compounds.

BRIEF SUMMARY

In a first aspect, the present invention is directed to a cosmetic emulsion having an aqueous continuous phase having: (a) at least one silicone resin, (b) at least one ethylenic polymer including a monomer having a bicyclic group, and (c) at least one taurate copolymer.

It is preferable that the (a) at least one silicone resin is a powder having an average particle size between about 20 microns and about 100 microns. The at least one silicone resin may be a silicone MQ resin. The silicone resin may advantageously be trimethylsiloxysilicate. Further, the at least one silicone resin may be present in the emulsion in a content ranging from about 2% to about 10% by weight.

It is preferable that the (b) at least one ethylenic polymer including a monomer having a bicyclic group is acrylic acid/isobutyl acrylate/isobornyl acrylate copolymer. The at least one ethylenic polymer including a monomer having a bicyclic group may be present in the emulsion in a content ranging from about 0.5% to about 3.5% by weight.

It is preferable that the (c) at least one taurate copolymer is acrylamide/sodium acryloyldimethyltaurate copolymer. The at least one taurate copolymer may be present in the emulsion in a content ranging from about 0.4% to about 2.8% by weight.

Advantageously, the ratio of the at least one ethylenic polymer including a monomer having a bicyclic group to the at least one silicone resin is between about 1:1 and about 1:2.

It is of further advantage for the ratio of the at least one taurate copolymer to the at least one silicone resin to be between about 1:1 and about 1:3. It is of still further advantage for the ratio of the sum of the at least one ethylenic polymer including a monomer having a bicyclic group and the at least one taurate copolymer to the at least one silicone resin be between about 1:1 and about 2:1.

The emulsion may also include at least one pigment, which may include mica. The at least one pigment may be present in the emulsion in a content ranging from about 5% to about 30% by weight.

The emulsion may also include at least one volatile alcohol, which may include denatured alcohol. The at least one volatile alcohol may be present in the emulsion in a content ranging from about 2% or about 8% by weight.

The emulsion may advantageously include at least two solvents. Preferably, at least one of the at least two solvents is a nonpolar solvent.

The emulsion may advantageously include at least one filler agent and may preferably include a filler agent having an average particle size of between about 1 micron and about 10 microns.

DETAILED DESCRIPTION

As used herein, articles such as "a" and "an" when used in a claim, are understood to mean one or more of what is claimed or described.

As used herein, the term "about [a number]" is intended to include values rounded to the appropriate significant digit. Thus, "about 1" would be intended to include values between 0.5 and 1.5, whereas "about 1.0" would be intended to include values between 0.95 and 1.05.

As used herein, the term "at least one" means one or more and thus includes individual components as well as mixtures/combinations.

As used herein, the term "ethylenic polymer" means a polymer obtained by polymerization of ethylenically unsaturated monomers.

As used herein, the terms "include", "includes" and "including" are meant to be non-limiting.

As used herein, the terms "O/W emulsion" or "oil-in-water emulsion" mean any macroscopically homogeneous composition comprising a continuous aqueous phase and a fatty phase dispersed in the said aqueous phase in the form of droplets.

As used herein, the term "volatile" means having a flash point of less than about 100° C.

The present invention is directed to a cosmetic emulsion having an aqueous continuous phase, the emulsion comprising: (a) at least one silicone resin, (b) at least one ethylenic polymer including a monomer having a bicyclic group, and (c) at least one taurate copolymer. Each of these will be discussed in turn.

The composition according to the present invention first includes at least one silicone resin. Typically, the at least one silicone resin is capable of functioning as a skin conditioning agent and/or an occlusive. If two or more silicon resins are used, they may or may not have the same INCI name.

In some embodiments, at least one silicone resin is a powder, preferably having an average particle size between about 1 micron and about 100 microns, and more preferably between about 20 microns and about 100 microns.

In some embodiments, at least one silicone resin is a silicone MQ resin. In some embodiments, the M:Q ratio in the silicone MQ resin is preferably between 0.5 and 2, and more preferably between 0.7 and 1.5. The silicone resin may advantageously be trimethylsiloxysilicate.

In some embodiments, at least one silicone resin is preferably present in the emulsion in a content ranging from about 1% to about 15% by weight, more preferably from about 2% to about 10%, and still more preferably from about 3% to about 5%.

In some embodiments, at least one silicone resin is soluble in a $C_{12}$-$C_{16}$ straight or branched chain hydrocarbon.

The composition also includes at least one ethylenic polymer including a monomer having a bicyclic group. Typically, the at least one ethylenic polymer including a monomer having a bicyclic group is capable of functioning as a film forming agent. If two or more ethylenic polymers including a monomer having a bicyclic group are used, they may or may not have the same INCI name.

In preferred embodiments, the bicyclic group is a bicyclic terpene group. In more preferred embodiments, the monomer having a bicyclic group is isobornyl acrylate (or methacrylate). In still more preferred embodiments, the ethylenic polymer is an acrylic acid/isobutyl acrylate/isobornyl acrylate copolymer.

In other embodiments, at least one ethylenic polymer including a monomer having a bicyclic group may be obtained from aliphatic ethylenic monomers. By aliphatic monomer is meant a monomer containing no aromatic group.

In preferred embodiments, the monomers that comprise the at least one ethylenic polymer including a monomer having a bicyclic group do not include silicon atoms in the main chain of the monomer.

Preferably, the at least one ethylenic polymer including a monomer having a bicyclic group is not water-soluble, or soluble in a mixture of water and linear or branched lower monoalcohols having 2 to 5 carbon atoms, such as ethanol, isopropanol or n-propanol, without a change in pH, at an active substance content of at least 1% by weight, at ambient temperature (25° C.).

In some embodiments, the at least one ethylenic polymer including a monomer having a bicyclic group comprises a monomer having a glass transition temperature ($T_g$) greater than 50 degrees C., and more preferably greater than 90 degrees C. In some embodiments, the at least one ethylenic polymer including a monomer having a bicyclic group comprises two or more monomers, each having a $T_g$ greater than 50 degrees C., and more preferably greater than 90 degrees C.

In various embodiments, the at least one ethylenic polymer including a monomer having a bicyclic group may be present in the emulsion in a content ranging from about 0.1% to about 5% by weight, more preferably from about 0.5% to about 3.5% by weight, and still more preferably from about 1% to about 2% by weight.

The composition also includes at least one taurate copolymer. Typically, the at least one taurate copolymer is capable of functioning as a thickening agent. These taurate copolymers may be hydrophilic and may contain an acrylate component. The at least one taurate copolymer may include, for example, acrylamide/sodium acryloyl dimethyl taurate copolymer, hydroxyethyl acrylate/sodium acryloyl dimethyl taurate copolymer, and/or sodium acrylate/sodium acryloyl dimethyl taurate copolymer. Preferably, the at least one taurate copolymer is obtainable from ethylenically unsaturated, sulpho-functional monomers and ethylenically unsaturated hydrophilic monomers, and more preferably from crosslinked anionic copolymers of acrylamide or methacrylamide and of 2-acrylamido-2-methyl-propanesulfonic acid.

In various embodiments, the at least one taurate copolymer may be present in the emulsion in a content ranging from about 0.1% to about 5% by weight, more preferably from about 0.4% to about 2.8% by weight, and still more preferably from about 0.6% to about 1% by weight.

Further, the ratio of the three components may be selected to provide desirable characteristics. In certain embodiments, it is advantageous to maintain the ratio of the at least one ethylenic polymer including a monomer having a bicyclic group to the at least one silicone resin to be between about 1:1 and about 1:4, and more preferably from a ratio of about 1:2 to about 1:3. In certain embodiments, it is advantageous to maintain the ratio of the at least one taurate copolymer to the at least one silicone resin to be between about 1:2 and about 1:6, and more preferably from a ratio of about 1:4 to about 1:6. In certain embodiments, it is advantageous for the ratio of the sum of the at least one ethylenic polymer including a monomer having a bicyclic group and the at least one taurate copolymer to the at least one silicone resin be between about 1:1 and about 1:4, and more preferably from a ratio of about 1:1.5 to about 1:2.5.

The present disclosure is drawn to an oil-in-water emulsion, and therefore comprises water. The amount of the water may be from 40 to 90% by weight, preferably from 45 to 80% by weight, and more preferably from 50 to 60% by weight, relative to the total weight of the composition.

Since the composition according to the present invention comprises water, the composition according to the present invention also comprises an aqueous phase as a continuous outer phase of the composition in the form of an O/W emulsion.

The aqueous phase may optionally comprise a volatile alcohol, which may include a $C_2$-$C_6$ monohydric alcohol. The $C_2$-$C_6$ monohydric alcohol suitable for the present invention may preferably comprise from 2 to 5 carbon atoms, and more preferably from 2 to 4 carbon atoms. Examples include, but are not limited to ethanol, isopropanol, propanol or butanol. The alcohol may be a denatured alcohol, including but not limited to SDA 29, 35, 35A, and/or 40. Further, two or more alcohols may be used in combination.

Ethanol and isopropanol, and preferably ethanol, are particularly suitable for the present invention.

The amount of the volatile alcohol in the composition according to the present invention may be 20% by weight or less, preferably 15% by weight or less, and more preferably 8% by weight or less, relative to the total weight of the composition. On the other hand, the amount of the $C_2$-$C_6$ monohydric alcohol in the composition according to the present invention is 1% by weight or more, preferably 1.5% by weight or more, and more preferably 2% by weight or more, relative to the total weight of the composition. For example, the amount of the volatile alcohol may be from 1% to 20% by weight, preferably from 1.5% to 15% by weight, and more preferably from 2% to 8% by weight, in relation to the total weight of the composition. Still more preferred are compositions comprising between 4% and 6% by weight of the volatile alcohol.

The aqueous phase may also comprise polyhydric alcohols containing 1 to 8 carbon atoms such as propylene glycol, ethylene glycol, 1,3-butylene glycol, dipropylene glycol, diethylene glycol, hexyleneglycol, glycerin, and mixtures thereof.

The amount of the polyhydric alcohol(s) such as glycols, if present, in the aqueous phase according to the present invention may range from 0.1 to 15% by weight, preferably from 0.5 to 12% by weight, and more preferably from 1 to 8% by weight, relative to the total weight of the composition.

The emulsion may also include at least one pigment. Typically, these pigments are inorganic. Examples of inorganic pigments include, but are not limited to, talc, mica, magnesium carbonate, calcium carbonate, magnesium silicate, aluminum magnesium silicate, silica, titanium dioxide, zinc oxide, red iron oxide, yellow iron oxide, black iron oxide, ultramarine, polyethylene powder, methacrylate powder, polystyrene powder, silk powder, crystalline cellulose, starch, titanated mica, iron oxide titanated mica, bismuth oxychloride, and the like. The aforementioned pigments can be used independently or in combination.

The at least one pigment may be present in the emulsion in a content ranging from about 1% to about 30% by weight, more preferably from about 5% to about 30% by weight, and still more preferably from about 15% to about 25%.

The emulsion may also include a plurality of solvents or oils in the oil phase. Such solvents or oils may include, but are not limited to, hydrocarbon oils, esters, and silicone oils. Preferably, at least one of the at least two solvents or oils is a nonpolar solvent. In some embodiments, each of the at least one solvents is a straight or branched chain saturated hydrocarbon comprising between 12 and 16 carbons. The plurality of solvents or oils may be present in the emulsion in a content ranging from about 1% to about 10% by weight, more preferably from about 3% to about 9% by weight, and still more preferably from about 5% to about 8%.

The emulsion may also include at least one filler agent. The filler agent and may preferably include a filler agent having an average particle size of between about 1 micron and about 10 microns. In some embodiments, the filler agent may include, but is not limited to inorganic powders such as amorphous silica, kaolin, sericite, muscovite, phlogopite, and synthetic mica.

The disclosed composition may also advantageously avoid the use of several types of polymers, including block copolymers, and specifically styrenic block copolymers.

The disclosed composition may also comprise one or more standard cosmetic adjuvants chosen from, for example, lipophilic thickeners, softeners, humectants, opacifiers, stabilizers, emollients, silicones, antifoams, fragrances, preserving agents, surfactants, active agents, colouring agents, cationic polymers, propellants, or any other ingredient usually used in cosmetics and/or dermatology.

A person skilled in the art will take care to select the optional adjuvant(s) added to the composition according to the present invention such that the advantageous properties intrinsically associated with the composition according to the invention are not, or are not substantially, adversely affected by the envisaged addition.

The composition according to the present invention may preferably be used as a cosmetic composition. In particular, the composition according to the present invention may be intended for application onto the skin, scalp and/or lips, preferably the skin, and in particular the skin around eyes. Thus, the composition according to the present invention can be used for a cosmetic process for the skin.

The cosmetic composition may be a skin care or skin makeup composition, for instance a foundation, a concealer, an eye makeup such as an eye shadow, or a body makeup, in particular, a foundation to be applied to the face and/or the neck, or an eye makeup to be applied around eyes.

Examples

The present invention will be described in a more detailed manner by way of examples. However, these examples should not be construed as limiting the scope of the present invention. The examples below are presented as non-limiting illustrations in the field of the invention.

Preparations

The following compositions according to Examples (Ex.) 1-3 and Comparative Example (Comp. Ex.) 1, shown in Table 1, were prepared by mixing the components shown in Table 1. Specifically, the Phase A ingredients were added to a first vessel and mixed until homogenous, then set aside. The Phase B-1 ingredients were then added to a new vessel and mixed until homogenous. The Phase B-2 ingredients are then added, and mixed until homogenous. The Phase B-3 ingredients are then added, and mixed until homogenous. The Phase B-4 ingredients are then added, and mixed until homogenous. The Phase B-5 ingredients are then added and mixed. Phase A is then added to combined Phase B, and mixed. Phase C is then added and mixed. The composition is then cooled and transferred as appropriate. The numerical values for the amounts of the components shown in Table 1 are all based on "% by weight".

TABLE 1

| | Ex. 1 | Ex. 2 | Ex. 3 | Comp. Ex. 1 |
|---|---|---|---|---|
| Phase A | | | | |
| Trimethylsiloxysilicate | 4 | 4 | 4 | 4 |
| Isododecane | 4 | 4 | 6 | 4 |
| Phase B-1 | | | | |
| Water | 54.6 | 54.6 | 52.9 | 54.6 |
| Glycols | 6.5 | 6.5 | 5.5 | 6.5 |
| Chelation Agent | 0.1 | 0.1 | 0.1 | 0.1 |
| Phase B-2 | | | | |
| Acrylamide/sollium acryloyldimethyltaurate copolymer (and) Isohexadecane (and) Polysorbate (40% Active) | 2 | 2 | 2 | — |
| PEG240/HDI Copolymer Bis-Decyltetradeceth-20 Ether | — | — | — | 2 |
| Phase B-3 | | | | |
| Filler Agent | 0.5 | 0.5 | 1 | 0.5 |
| Phase B-4 | | | | |
| Pigments | 20 | 20 | 20 | 20 |
| Phase B-5 | | | | |
| Preservative | 0.3 | 0.3 | 0.5 | 0.3 |
| Alcohol Denatured | 5 | 5 | 5 | 5 |
| Phase C | | | | |
| Acrylic Acid/Isobutyl Acrylate/Isobornyl Acrylate Copolymer (50% Active) | 3 | 3 | 3 | 3 |

Examples 1-3 are stable and can provide all the target cosmetic effects (squeezable formulation, forms a soft cosmetic film, has uniform adhesion to skin and provides long lasting effect). On the other hand, Comparative Example 1 was not stable.

Those skilled in the art will recognize, or be able to ascertain using no more than routine experimentation, many equivalents to the specific embodiments of the invention described herein. Such equivalents are intended to be encompassed by the following claims.

What is claimed is:

1. A oil-in-water emulsion having an aqueous continuous phase, the emulsion comprising:
   - at least one silicone resin;
   - at least one ethylenic polymer including a monomer having a bicyclic group; and
   - at least one taurate copolymer,
   - wherein the ratio of the at least one ethylenic polymer including a monomer having a bicyclic group to the at least one silicone resin is between about 1:2 and about 1:3, and
   - wherein the emulsion does not contain any block copolymers, and wherein the emulsion is in the form of an eye makeup.

2. The emulsion according to claim 1, wherein the emulsion comprises:
   - from about 2% to about 10% by weight of the at least one silicone resin:
   - from about 0.5% to about 3.5% by weight of the at least one ethylenic polymer including a monomer having a bicyclic group; and
   - from about 0.4% to about 2.8% by weight of the at least one taurate copolymer.

3. The emulsion according to claim 1, further comprising at least one pigment.

4. The emulsion according to claim 3, wherein the emulsion comprises from about 5% to about 30% by weight of at least one pigment.

5. The emulsion according to claim 1, further comprising at least one volatile alcohol.

6. The emulsion according to claim 5, wherein the emulsion comprises from about 2% to about 8% by weight of the at least one volatile alcohol.

7. The emulsion according to claim 5, wherein the volatile alcohol is denatured alcohol.

8. The emulsion according to claim 1, wherein the at least one silicone resin is a silicone MQ resin.

9. The emulsion according to claim 1, wherein the at least one silicone resin is trimethylsiloxysilicate.

10. The emulsion according to claim 1, wherein the at least one ethylenic polymer including a monomer having a bicyclic group is acrylic acid/isobutyl acrylate/isobornyl acrylate copolymer.

11. The emulsion according to claim 1, wherein the at least one taurate copolymer is acrylamide/sodium acryloyldimethyltaurate copolymer.

12. The emulsion according to claim 1, further comprising at least two solvents, wherein the at least two solvents are present in a total amount from about 5% to about 8% by weight.

13. The emulsion according to claim 12, wherein at least one of the at least two solvents is a nonpolar solvent.

14. The emulsion according to claim 1, further comprising at least one filler agent.

15. The emulsion according to claim 13, wherein the at least one filler agent has an average particle size of between about 1 micron and about 10 microns.

16. The emulsion according to claim 1, wherein the ratio of the at least one taurate copolymer to the at least one silicone resin is between about 1:4 and about 1:6.

17. The emulsion according to claim 16, wherein the ratio of the sum of the at least one ethylenic polymer including a monomer having a bicyclic group and the at least one taurate copolymer to the at least one silicone resin is between about 1:1.5 and about 1:2.5.

18. The emulsion according to claim 1, wherein the at least one ethylenic polymer is obtained from aliphatic ethylenic monomers.

19. The emulsion according to claim 1, wherein the at least one silicone resin is soluble in a C12-C16 straight or branched chain hydrocarbon.

20. The emulsion according to claim 5, further comprising a plurality of polyhydric alcohols, wherein the plurality of polyhydric alcohols are present in the emulsion in a total amount from 1% to 8% by weight.

* * * * *